US012714443B2

(12) United States Patent
Asfora

(10) Patent No.: US 12,714,443 B2
(45) Date of Patent: Aug. 25, 2026

(54) SURGICAL BONE DRILL

(71) Applicant: Asfora IP, LLC, Sioux Falls, SD (US)

(72) Inventor: Wilson Theophilo Asfora, Sioux Falls, SD (US)

(73) Assignee: Asfora IP, LLC, Sioux Falls, SD (US)

( * ) Notice: Subject to any disclaimer, the term of this patent is extended or adjusted under 35 U.S.C. 154(b) by 0 days.

(21) Appl. No.: 18/420,353

(22) Filed: Jan. 23, 2024

(65) Prior Publication Data

US 2024/0245409 A1 Jul. 25, 2024

Related U.S. Application Data

(60) Provisional application No. 63/481,071, filed on Jan. 23, 2023.

(51) Int. Cl.
*A61B 17/16* (2006.01)

(52) U.S. Cl.
CPC ...... *A61B 17/1633* (2013.01); *A61B 17/1615* (2013.01)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1633; A61B 17/1655; A61B 17/1657; A61B 17/1695
See application file for complete search history.

(56) References Cited

U.S. PATENT DOCUMENTS 3,682,177 A * 8/1972 Ames ................. A61B 17/1695 408/202
5,810,828 A * 9/1998 Lightman ............. B23B 49/008 606/80
6,739,872 B1 * 5/2004 Turri ...................... A61B 17/16 408/202
6,923,799 B1 * 8/2005 Asfora .................... A61M 1/82 604/541
7,210,881 B2 * 5/2007 Greenberg ......... A61B 17/1615 408/202

(Continued)

FOREIGN PATENT DOCUMENTS

CN 111528976 A * 8/2020
WO WO-9835621 A1 * 9/1998 ........... A61B 17/164

(Continued)

*Primary Examiner* — Eric S Gibson
(74) *Attorney, Agent, or Firm* — Fox Rothschild LLP

(57) ABSTRACT

A surgical bone drill for drilling into bones. The surgical bone drill includes a housing, a drill bit that includes a bit proximal portion that is mounted within the housing, and a bit distal portion that extends distally from the housing and includes a cutting tip. The surgical bone drill includes a depth limiter that has a distal end positioned adjacent the bit distal portion. A location of the depth limiter is adjustable with respect to the housing to select an exposed length of the bit distal portion that is exposed beyond the depth limiter, thereby limiting a depth that the drill bit can drill into the bone. The surgical bone drill includes a drive mechanism disposed within the housing and operably connected with the bit proximal portion of the drill bit to rotate the drill bit to cause the drill to drill into the bone.

23 Claims, 5 Drawing Sheets

(56) References Cited

U.S. PATENT DOCUMENTS 7,553,290 B1 * 6/2009 Asfora .................. A61B 5/031 604/93.01
7,569,058 B2 * 8/2009 Zwirnmann ....... A61B 17/1655 606/80
7,694,821 B1 * 4/2010 Asfora .................. A61B 50/33 604/27
8,834,417 B2 * 9/2014 Moos .................. A61B 10/025 604/117
9,861,373 B2 * 1/2018 Kfir .................... A61B 17/1604
11,065,033 B2 * 7/2021 Kalhorn ............. A61B 17/3496
11,154,308 B2 * 10/2021 Khosla .................. A61B 90/03
11,529,147 B2 * 12/2022 Frey ...................... A61B 17/17
2005/0147478 A1 * 7/2005 Greenberg ......... A61B 17/1615 408/241 S
2006/0004372 A1 * 1/2006 Zwirnmann ....... A61B 17/1633 606/80
2007/0055249 A1 * 3/2007 Jensen ............... A61B 17/8863 606/288
2008/0051793 A1 * 2/2008 Erickson ............ A61B 17/1671 606/279
2009/0264811 A1 * 10/2009 Asfora ............. A61M 39/0247 604/28
2011/0152866 A1 * 6/2011 Knutson ............ A61B 17/3472 606/86 R
2014/0276880 A1 * 9/2014 Li .......................... A61B 17/17 606/96
2015/0289886 A1 * 10/2015 Kfir .................... A61B 17/1604 606/84
2017/0291017 A1 * 10/2017 Branch, Jr. ......... A61M 25/002
2018/0161124 A1 * 6/2018 Huwais ................. B23B 49/005
2021/0045754 A1 * 2/2021 Khosla ............... A61B 17/1633
2022/0039808 A1 * 2/2022 Frey ................... A61B 17/1615
2023/0117196 A1 * 4/2023 Frey ...................... A61B 17/16 408/202
2024/0099728 A1 * 3/2024 King ...................... A61B 90/03
2024/0245409 A1 * 7/2024 Asfora ............... A61B 17/1633

FOREIGN PATENT DOCUMENTS

WO WO-2005065377 A2 * 7/2005 ......... A61B 17/1615
WO WO-2016098976 A1 * 6/2016 ............. A61B 17/16
WO WO-2021003154 A1 * 1/2021 ....... A61B 17/00234
WO WO-2021030398 A1 * 2/2021 ......... A61B 17/1633
WO WO-2022170152 A1 * 8/2022 ............. A61B 17/16

* cited by examiner

SURGICAL BONE DRILL

CROSS-REFERENCE TO RELATED APPLICATIONS

The present application claims the benefit of U.S. Provisional Patent Application No. 63/481,071, filed Jan. 23, 2023, which is incorporated herein by reference in its entirety.

FIELD OF THE DISCLOSURE

The present disclosure relates to a surgical bone drill and, more particularly, relates to surgical bone drills for use in drilling bones that have soft tissue beyond the bone being drilled.

BACKGROUND

The human skeleton consists of many kinds of bones including, upper and lower jawbones and spine or skull, that can have, for example, various thicknesses and surrounding materials. In many surgical treatments or therapies, it is desired to provide one or plural holes into a bone of a patient. Depending on the location, thickness, and surrounding materials such as membrane linings and other soft tissues, drilling the bone can present various challenges.

Many tools such as drills are used for various drill procedures. Conventional drill bits can be applied where there is sufficient bone depth or in locations where other important anatomy such as membranes, nerves or cells are not present. However, in cases where the bone density is light, bone thickness is thin, or other important parts such as the membranes, nerves or cells are present, it is required to drill such that no damage is done to these other important parts. This presents challenges to even the most skillful users of the drill. While conventional drill bits may easily penetrate the bone, the tips of the drill blades can damage the membrane by tearing or rolling when the tip of the drill contacts the membrane. Furthermore, previous approaches have utilized a drill bit that needed a pilot drill or bur to initiate the cut in the bone.

For example, in many surgical operations it is necessary to obtain direct access to the cranial cavity and the brain underneath the skull bone. To perform such operations, it is often necessary to drill holes through the skull bone. Since the bone is very hard, it is necessary to apply significant pressure to drill through the bone, but it is also necessary to stop the drill once the bone has been penetrated to prevent damage to the soft tissue underneath.

BRIEF SUMMARY OF THE INVENTION

The present disclosure relates to systems, methods, and devices for drilling into bone of a patient.

According to the present disclosure, in certain scenarios, a surgical bone drill may include a housing and a drill bit. The drill bit may include a bit proximal portion that is mounted within the housing, and a bit distal portion that extends distally from the housing and includes a cutting tip configured to drill into bone of a patient. The surgical bone drill may also include a depth limiter having a distal end positioned adjacent the bit distal portion. A location of the depth limiter is adjustable with respect to the housing to select an exposed length of the bit distal portion that is exposed beyond the depth limiter. The depth limiter thereby limits a depth that the drill bit is able to drill into the bone. The surgical bone drill additionally may include a drive mechanism disposed within the housing and operably connected with the bit proximal portion of the drill bit to rotate the drill bit to cause the drill to drill into the bone.

In certain implementations, the surgical bone drill may further include a locking nut configured to prevent rotation of the depth limiter after the exposed length of the bit distal portion is selected. In certain implementations, the depth limiter is affixable relative to the housing.

In various implementations, the housing of the surgical drill may include a sleeve configured to receive the bit proximal portion. In such implementations, the depth limiter may include an adjustment collar that is adjustably threaded onto the sleeve to enable adjustment of the exposed length. Optionally, the adjustment collar may include a limiter distal portion having a first height and a first width and positioned adjacent the bit distal portion, and a limiter proximal portion having a second height and a second width. The limiter distal portion is configured to abut the patient. The first height and the first width of the bit distal portion are less than the second height and the second width of the limiter proximal portion.

In some examples, the cutting tip of the drill bit may be a convex conical cutting tip with a spike extending distally from the cutting tip, the spike being sufficiently sharp to pierce a dura of the patient.

According to another scenario, the present disclosure relates to a surgical bone drill that may include a housing, a drill bit including a cutting tip configured to drill into bone of a patient, and a depth limiter mounted to the housing. The depth limiter may be configured to select an exposed length of drill bit that is exposed beyond the depth limiter which thereby limits a depth that the drill bit drills into the bone. The depth limiter may include a limiter distal portion having a first width and a first height, and being positioned adjacent the exposed length of drill bit, and a limiter proximal portion having a second width and a second height. The first width and the first height of the limiter distal portion is smaller than the second width and the second height of the limiter proximal portion. The surgical drill may also include a drive mechanism operably connected with a proximal portion of the drill bit to rotate the drill bit to cause the drill to drill into the bone without rotation of the depth limiter.

Optionally, the depth limiter may taper between the limiter proximal portion and the limiter distal portion. Additionally, and/or alternatively, the limiter proximal portion may terminate distally at a limiter distal end which is smooth and configured to abut the patient.

In certain implementations, the limiter proximal portion may be adjustable with respect to the housing to select the exposed length of drill bit that is exposed beyond the depth limiter and the limiter distal portion is adjacent to the exposed length of drill bit.

In certain implementations, the housing of the surgical drill may include a sleeve configured to receive the bit proximal portion. Additionally, the depth limiter may include an adjustment collar that is adjustably threaded onto the sleeve to enable adjustment of the exposed length.

In various implementations, the drill bit may include a bit distal portion which includes a convex conical cutting tip with a spike extending distally from the cutting tip. The spike is sufficiently sharp to pierce a dura of the patient.

The surgical bone drill can further include a locking nut configured to prevent rotation of the depth limiter after the exposed length of the bit distal portion is selected.

In some examples, the drill bit includes a bit proximal portion that is mounted within the housing, and a bit distal portion that extends distally from the housing. In some cases, the depth limiter surrounds the bit distal portion.

The present disclosure additionally discloses scenarios that relate to a cranial drill bit. The cranial drill bit may include an elongated body. The elongated body includes a bit distal portion which has a cutting tip configured to drill into bone of a patient, a cutting flute that extends proximally from the cutting tip. The cutting flute may be configured to remove material as the cutting tip drills into the bone of the patient. Additionally, the cranial drill bit may include a spike extending distally from the cutting tip and terminating at a point, wherein the spike is configured to cut a dura of the patient, and the spike is smaller than the cutting tip.

In certain implementations, the spike of the cranial drill bit may include the cutting flute.

In certain implementations, the cranial drill bit may be included in any of the surgical drills as discussed above.

Additionally, the present disclosure discloses scenarios relating to a surgical kit. The surgical kit may include any of the surgical bone drills discussed herein and other components such as one or more devices for evacuation of fluid from a subdural space of the patient.

For example, the one or more devices for evacuation of fluid from the subdural space may include: a subdural evacuation port device, and a negative pressure device.

In some cases, the kit may also include a tapper for creating threads within a hole created by the drill.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DETAILED DESCRIPTION OF THE INVENTION

Figure 1:
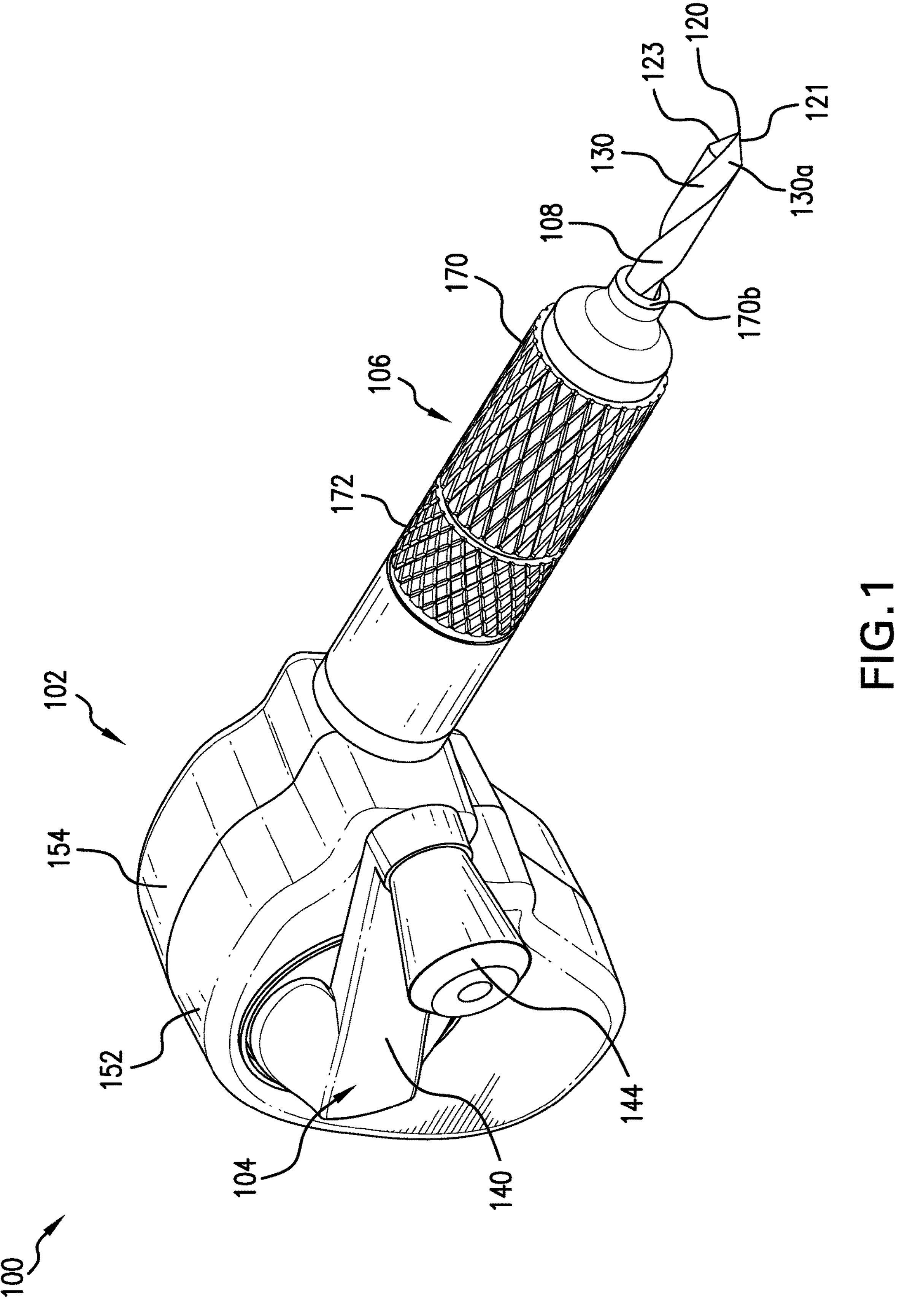
FIG. 1 is a perspective view of a surgical drill in accordance with the principles of the present disclosure.

The subdural space of the human head is the space located between the brain and the lining of the brain, which is referred to as the dura mater (hereinafter referred to as the "dura"). Hemorrhages on the surface of the brain, for example, may cause a condition known as a subdural hematoma. The subdural hemorrhages may have a number of causes. For example, elderly persons may be more susceptible to subdural hemorrhages because as the brain ages it tends to become atrophic and the subdural space between the brain and the dura gradually enlarges. Bridging veins between brain and dura frequently stretch and rupture as a consequence of relatively minor head injuries, thus giving rise to a collection of blood in the subdural space. Further, severe linear acceleration or deceleration of the brain can result in the brain moving excessively with respect to the dura, often causing rupture of the bridging veins or the blood vessels on the surface of the brain, which can cause subdural hemorrhages in an otherwise healthy brain. Since the subdural hematomas primarily comprise collections of liquid, the treatment may range from the performance of a craniotomy to the use of a burr hole (depending upon severity), that each require creating hole(s) in the skull (e.g., using a drill). An example of a process for evacuating subdural space after the subdural space has been accessed is described in U.S. Pat. No. 7,694,821.

For example, for creating hole(s) in the skull to access the subdural space of a human brain, a drill drills a hole into a patient's skull. Once the hole is drilled, the dura of the brain is punctured to allow access to the subdural space. However, existing drills use a relatively dull drill bit which can push on the dura and can lead to complications. Moreover, multiple instruments may be required after the drill has drilled the hole to puncture the dura (e.g., a needle, stylet, or other device can be used to puncture the dura) adding additional complexity. Finally, to achieve a precise depth that the drill bit drills into the patient's skull a depth limiter and/or drill stop is used for the precise depth (drill stop and depth limiter are used interchangeably herein). Such a depth limiter is attached to the drill bit and rotates with the drill bit requiring an incision large enough for the depth limiter and drill bit to be made in a human scalp prior to boring the hole into the skull creating a larger hole than is needed for the surgical treatment itself.

The present disclosure relates to systems that facilitate precisely drilling bones and penetrating other desired tissue without damaging surrounding tissue, such as soft tissue opposing the bone being drilled. Examples can include, but are not limited to, the skull, spine, the maxillary sinus area, and other bones adjacent to soft tissue. For example, the systems of the current disclosure can be used for accessing the subdural region of a subject and more particularly pertains to a surgical bone drill which can be used for accessing the subdural region of a subject in a manner that is minimally invasive. The surgical bone drill of the current disclosure can be used without the use of a pilot drill while protecting the soft tissue opposing the bone being drilled.

Figure 2:
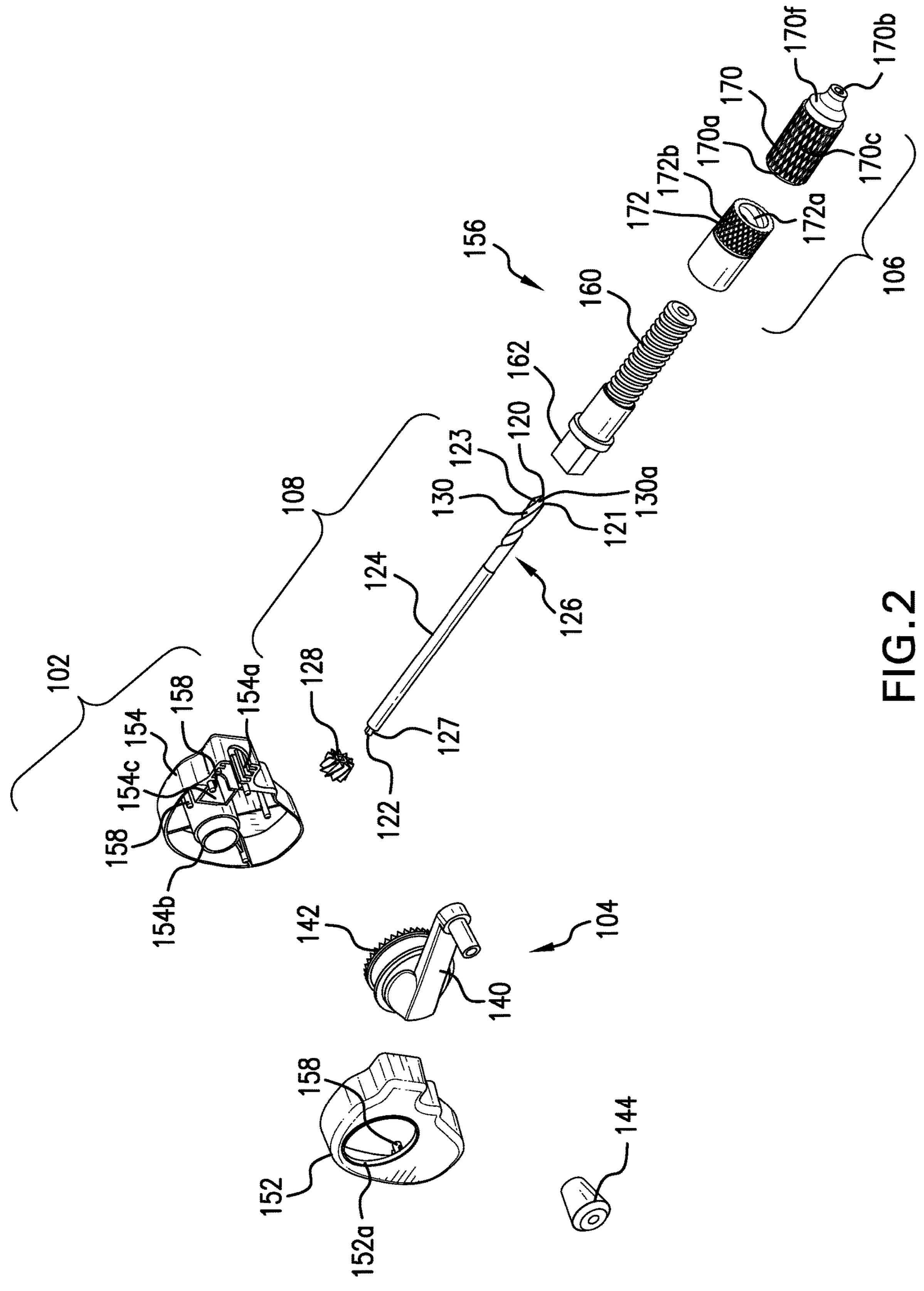
FIG. 2 is an exploded view of the surgical bone drill of FIG. 1.
Figure 3:
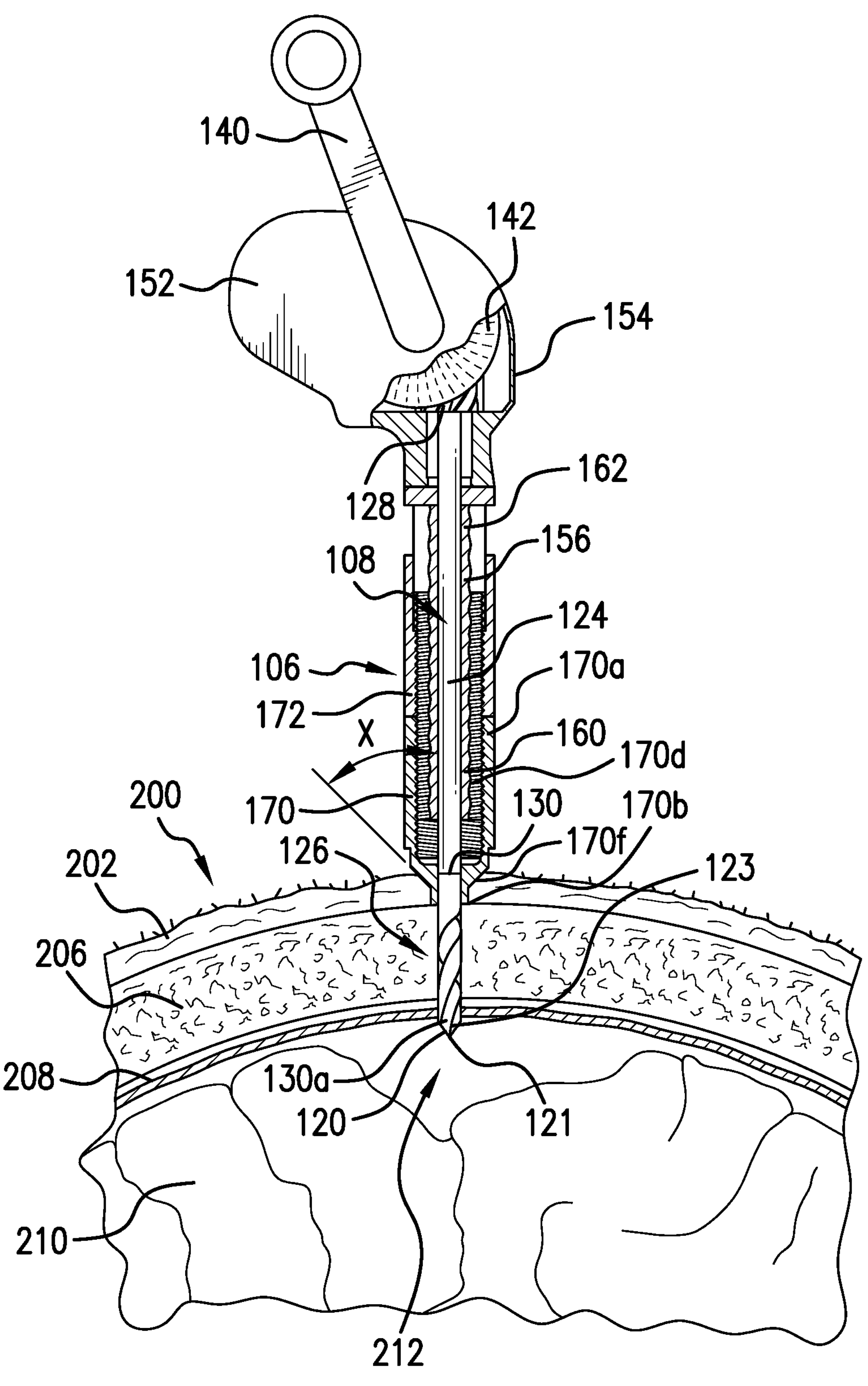
FIG. 3 is a sectional view of the surgical bone drill of FIG. 1 in use.

FIGS. 1-3 depict a surgical bone drill 100 in accordance with the principles of the present disclosure. The surgical bone drill 100 includes a housing 102, a drive mechanism 104, a depth limiter 106, and a drill bit 108. The drill bit 108 is rotatably mounted within the housing 102 and the depth limiter 106 is affixed directly to the housing 102 to allow the drill bit 108 to rotate without causing rotation of the depth limiter 106.

The term "drill bit" as used herein can relate to a longitudinal rotatable piece adapted to be mounted to a drilling device (e.g., surgical bone drill 100) and rotated by a drive mechanism of the surgical bone drill 100. The drill bit 108 has a rod like or cylindrical form wherein the circumference is profiled in a particular manner allowing for the drill bit to drill into bone. Alternatively, the drill bit 108 may have a different profile that allows for rotation and drilling, such as having a square, rectangular, prismatic, or other suitable cross-sectional shape. The drill bit is made of a hard material suitable for cutting or otherwise drilling into bone or the material that is being drilled through allowing the surgical bone drill 100 to create holes. In some examples, the drill is formed from a metal, e.g., surgical steel or other stainless steels, high-speed steel, or tungsten carbide, or a ceramic. The drill bit might be coated with a suitable material to aid chip evacuation, to provide a hard exterior surface, or for other purposes. Such coating material can include, for example, diamond-like carbon (DLC), titanium nitride (TiN) or other materials and or layers.

Referring to FIGS. 1-3, an embodiment of a drill bit 108 has an elongated, longitudinal body extending along an axis and having a proximal end 122 and a distal end 120, such that the body of the drill bit 108 extends between the distal end 120 and the proximal end 122. The drill bit 108 includes a bit proximal portion 124 extending from a flute(s) towards the proximal end 122. In this embodiment, the bit proximal portion has a smooth exterior profile which allows for the bit proximal portion to rotate smoothly within the housing, although other bits can have different exterior profiles and be sized to rotate within the housing. The flutes in this embodiment are spiral flutes. Other embodiments can have a longitudinal flute(s) that is parallel to the longitudinal axis, or other configurations suitable for cutting in a drilling operation. The drill bit 108 additionally includes a bit distal portion 126 towards the distal end 120. The bit distal portion 126 of the drill bit 108 includes a cutting portion 130 formed at the distal end 120 of the body that includes a main cutting face 130*a* extending from a cutting tip 123. In some examples, the bit distal portion 126 of the drill bit 108 also includes spiral flute(s) formed around the body and extending from the main cutting face along the axis of the body and towards the proximal end 122 (discussed below in more detail).

The bit proximal portion 124 extends into and is rotatably anchored within the housing 102 while the bit distal portion 126 extends out of the housing 102. Specifically, the bit proximal portion 124 is configured to operably connect with the drive mechanism 104, via one or more linkages (discussed below). In certain examples, the bit proximal portion 124 includes a connection interface 127 which operably connects the bit proximal portion 124 to the drive mechanism 104. In certain examples, the connection interface 127 is configured to be connected to or interface with a rotational coupling 128. In certain examples, the rotational coupling 128 is a bit gear. In certain examples, the bit gear is a pinion. Other types of gears are additionally possible such as a worm gear, a screw gear, a bevel gear or a different suitable gear. Other rotational couplings are within the scope of this disclosure such as, without limitation, a threaded coupling, a belt interface, or a different suitable rotational coupling. In certain examples, the rotational coupling 128 interface is separate from the drill bit 108, however, it will be appreciated that the rotational coupling 128 interface can be integrally formed with the drill bit 108. It will also be appreciated that the bit proximal portion 124 can engage with the drive mechanism 104 in other ways, for example, the bit proximal portion 124 can engage with a belt or a different suitable engagement interface if, for example, the drive mechanism 104 included a belt. In some examples, the rotational coupling 128 and the drill bit 108 are formed from different materials. In other examples, the rotational coupling 128 and the drill bit are unitary or formed from a similar material. In some examples, the drill bit 108 is formed from a metallic material and the rotational coupling 128 is formed from a polymer. In some examples, the rotational coupling 128 is formed from acrylonitrile butadiene styrene (hereinafter: ABS); Polycarbonate; Polypropylene; Nylon; or other suitable materials.

The bit distal portion 126 of the drill bit 108 includes a cutting portion 130. The cutting portion 130 includes a flute. Flutes are sharp slots that corkscrew upwards along the length and are responsible for cutting and ejecting bone chips as the drill bit 108 rotates. In certain examples, the cutting portion 130 includes two flutes. More or less flutes are additionally possible. The cutting portion 130 includes a cutting tip 123 that terminates at a spike 121 at the distal end 120. In some embodiments, the cutting tip 123 has an angle of about 5 degrees, about 10 degrees, about 15 degrees, about 20 degrees, about 25 degrees, about 30 degrees, about 35 degrees, about 40 degrees or any other suitable angle from opposite surfaces of the cutting tip. In some examples, the cutting tip has an angle of about 5-40 degrees, about 10-35 degrees, about 15-30 degrees, about 20-25 degrees, 25-30 degrees, or any other suitable range. The cutting tip 123 in combination with the spike 121 are configured to initiate drilling into bone of a patient by application of pressure without engagement of the drive mechanism 104, thereby allowing the surgical bone drill 100 to grip the bone and preventing slippage (without the use of additional tools such as a pilot drill). In certain embodiments, the spike 121 additionally limits slippage and grips the bone. In certain examples, the spike 121 is additionally configured to pierce the dura of a patient (discussed below). In some examples, the spike 121 is shaped conically and forms a tip angle of about 5 degrees, about 10 degrees, about 13 degrees, about 15 degrees, about 20 degrees, as measured from opposite surfaces of the spike 121. In other examples, the tip angle has a range of about 5-20 degrees, about 7-18 degrees, about 9-16 degrees, about 11-14 degrees, or any other suitable range. In other embodiments, the spike 121 is spear shaped. The spike 121 is sufficiently sharp to cut into the bone as the drill bit 108 is rotated and sharp enough to puncture tissue such as the dura 208. In some embodiments, the spike 121 is integrally formed with the drill bit 108 such that the drill bit 108 tapers into the spike 121 at a fine point. In some examples, the maximum diameter of the drill bit 108 is about 5 mm, about 5.5 mm, about 6 mm, about 6.5 mm, about 7 mm or any other suitable maximum diameter. In some examples, the maximum diameter of the drill bit 108 is between about 5 mm-7 mm, about 5.3 mm-6.7 mm, about 5.5 mm-6.5 mm, about 5.7 mm-6.3 mm, about 5.9 mm-6.1 mm, or any other suitable range of maximum diameters.

Figure 5:
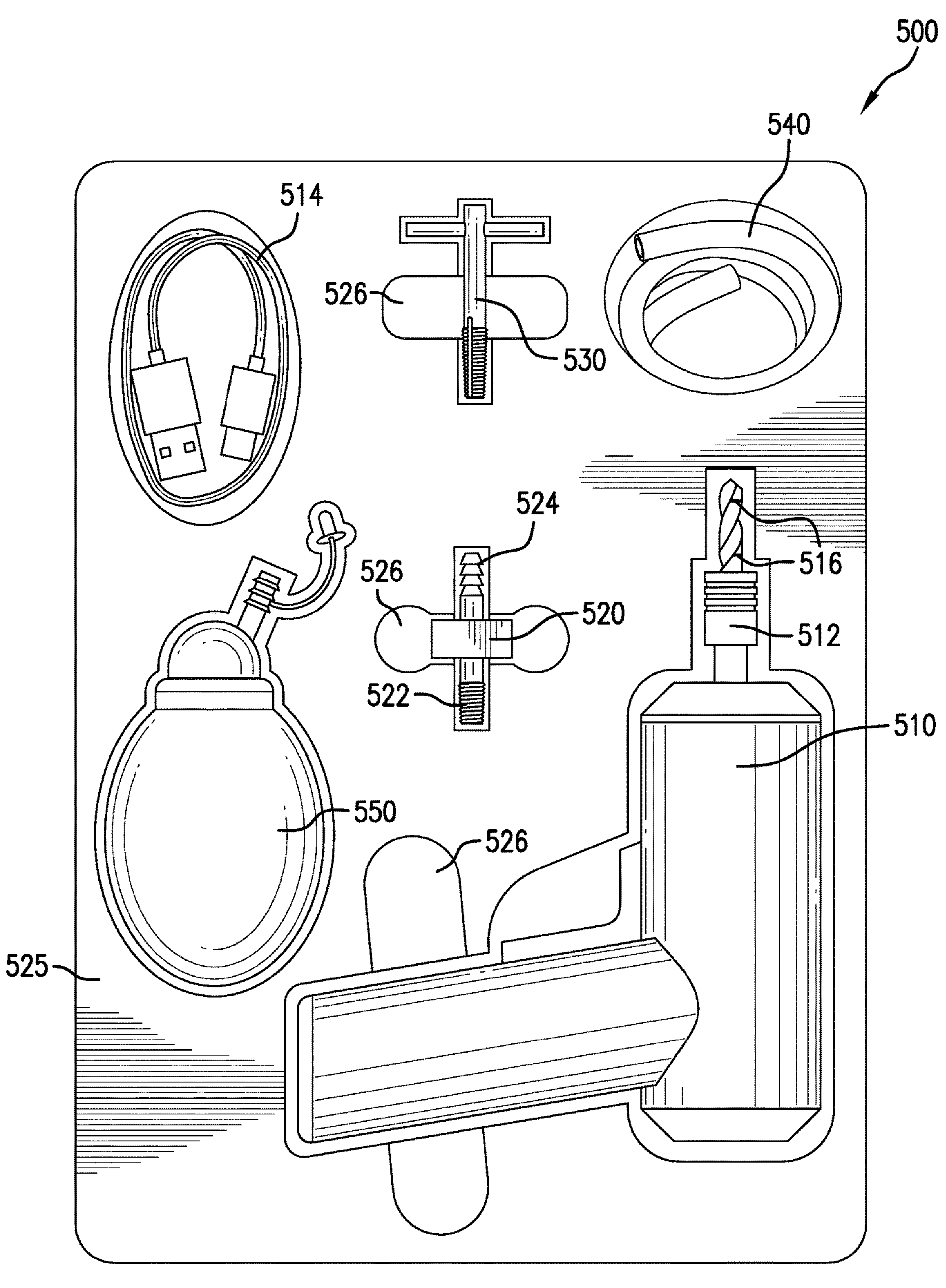
FIG. 5 is a top view of a kit including another embodiment of a surgical drill in accordance with the principles of the present disclosure.

Referring to FIG. 2, the drive mechanism 104 of the surgical bone drill 100 is operably connected to or interfaces with the bit proximal portion 124, and is configured to rotate the drill bit 108. The drive mechanism 104 is configured to be manually driven (e.g., an operator causes the drive mechanism 104 to rotate the drill bit 108 by rotation of a handle, crank, a similar manual rotator, via one or more linking mechanisms) or motor operated (e.g., as shown in FIG. 5, in which a motor causes the drive mechanism 104 to rotate the drill bit 108).

In FIG. 2, the drive mechanism 104 is a manually driven drive mechanism and includes a crank 140 attached to a rotational coupling 142 that interfaces with the drill bit 108 via the rotational coupling 128 of the drill bit 108. Types of rotational coupling 142 can include, without limitation, a gear, a belt, or a similar suitable rotational coupling. For example, the rotational coupling 142 can be a rack type gear including a plurality of teeth that are configured to engage with teeth included in the rotational coupling 128 of the bit proximal portion 124 such that rotation of the crank 140 causes rotation of the drill bit 108. While FIG. 2 illustrates the rotational coupling 142 having a rotational axis that is perpendicular to that of the rotational coupling 128, the disclosure is not so limiting, and other interface angles are within the scope of this disclosure. Optionally, the crank 140 includes an outer grip 144 which reduces hand slippage while a user is rotating the crank 140. The drive mechanism 104 can be formed from any suitable material. In some examples, the drive mechanism 104 is formed from a polymer. In some examples, the drive mechanism 104 is formed from ABS, Nylon, Polypropylene, or any other suitable material.

In embodiments including an electric motor the motor can be powered using a suitable power source, such as a battery, a power cable, an AC power source, a DC power source, a docking station, or any other suitable power source. In certain examples, the power source can be a rechargeable battery, a disposable battery or may be a single use battery. It will be appreciated that the motor may be powered by any other suitable mechanism that generates sufficient torque for the drill to create a hole. Other embodiments can use pneumatic motors or motors powered by other suitable types of sources.

The housing 102 of the surgical bone drill 100 is configured to contain the bit proximal portion 124 and the drive mechanism 104 such that the drive mechanism 104 is operably connected to the bit proximal portion 124. In certain examples, the housing 102 is a multi-piece housing. Alternatively, the housing 102 can be configured as a single piece housing. In the example of FIG. 2, the housing 102 includes three pieces, however the housing 102 can be a molded single piece housing, a two-piece housing (e.g., a clamshell housing), or a housing having more than three pieces.

The housing 102 includes a first housing portion 152, a second housing portion 154, and a sleeve 156. The first housing portion 152 and the second housing portion 154 include connectors 158 for attaching the first housing portion 152 to the second housing portion 154. In certain examples, the connectors 158 are snap fit connectors. In other examples, the first and second housing portions 152, 154 can connect via fasteners or other suitable attachment mechanism. The sleeve 156 includes a sleeve distal portion 160 and a sleeve proximal portion 162. The sleeve proximal portion 162 is received within the first and second housing portions 152, 154 and the sleeve distal portion 160 receives the bit proximal portion 124 which extends at least partially into the sleeve proximal portion 162 into the housing 102. The bit distal portion 126 extends distally out of the sleeve. The sleeve proximal portion 162 includes a connection interface which allows the sleeve 156 lock between the first and the second housing portions 152, 154. It will be appreciated that if the housing 102 was, for example, a two-piece housing a portion (e.g., half) of the sleeve 156 could be configured to be received within or interface with the first housing portion 152 and a portion (e.g., half) of the sleeve 156 could be configured to be received within or interface with the second housing portion 154. In certain embodiments, the sleeve proximal portion 162 is received within a slot 154*a* of the second housing portion 154. In some examples, the housing is made from a polymer. In some examples the housing is made from ABS Polycarbonate; Polypropylene; Nylon; or other suitable materials.

The first housing portion 152 includes an opening 152*a*. The opening 152*a* is sized such that at least a portion of the drive mechanism 104 can fit within the opening 152*a*, with the crank 140 extending out of the first housing portion 152 allowing for an operator to rotate the crank 140 thereby rotating the rotational coupling 142 and the drill bit 108. The rotational coupling 142 extends within the housing 102. The second housing portion 154 includes a circular portion 154*b*. The circular portion 154*b* can receive at least a portion of the drive mechanism 104 and allow the drive mechanism 104 to rotate within the housing 102 and engage the bit proximal portion 124 (via the rotational coupling(s)) to rotate the drill bit 108. In certain examples, the gear includes a reciprocal opening that can extend around the circular opening thereby allowing for rotation.

As discussed above, the sleeve 156 is configured to receive the bit proximal portion 124. The bit proximal portion 124 extends through the sleeve 156 and between the first and second housing portions 152, 154. In certain examples, the bit proximal portion 124 extends into only the second housing portion 154. The proximal end 122 of the drill bit 108 extends into a slot 154*c* in the second housing portion 154. The slot 154*c* is configured to allow the rotational coupling 142 of the drive mechanism 104 to engage with the rotational coupling 128 of the drill bit 108 such that when the drive mechanism 104 rotates, the drill bit 108 rotates. It will be appreciated that although only a portion of the drive mechanism 104 is shown extending into the housing 102, in other examples the entire drive mechanism 104 can be configured to fit within the housing 102.

In various embodiments, the surgical drill 100 also includes a depth limiter 106 configured to selectively control a length of the bit distal portion 126 that is exposed or extends from the housing 102 thereby limiting the depth that the bit distal portion 126 extends into the skull 206 of a patient. In some examples, the depth required for the procedure that the bit distal portion 126 extends into the skull 206 is determined by magnetic resonance imaging (MRI), computerized tomography scan (CT scan), or X-ray or a different method of generating images within the body of a patient.

In certain embodiments, the depth limiter 106 is mounted directly to the housing 102 (as depicted, the depth limiter 106 is mounted to the sleeve 156 of the housing 102). In certain examples, the depth limiter 106 is affixable relative to the housing 102. In certain examples, the depth limiter 106 is affixable and adjustable relative to the housing 102. In certain examples, the depth limiter 106 is affixed to the sleeve 156 of the housing 102. The depth limiter 106 can be affixed to the housing 102 in any applicable manner that allows for selection of length of the exposed bit distal portion 126, without causing rotation of the depth limiter 106 when the drill bit 108 is rotated at least until the depth limiter 106 contacts or abuts the surface (the skull 206) which the depth is limited through. For example, the sleeve distal portion 160 includes threads and the depth limiter 106 includes reciprocal threading that allows for the depth limiter 106 to be mounted to the sleeve 156 at a desired location. In some embodiments, the location of the mounted depth limiter 106 can be changed up or down the sleeve 156 by rotation of the depth limiter 106 over the threads of the sleeve distal portion 160. Based on the depth selected for insertion of the drill bit 108 within the skull 206 (e.g., from the MRI or X-ray above), the depth limiter 106 can be adjusted to a desired position over the sleeve 156, which in turn exposes a desired length of the bit distal portion 126 that allows drilling to the selected depth only. In other examples, the depth limiter 106 can be affixed to the housing sleeve 156 by a ratchet or other suitable mechanisms. It will be appreciated that the depth limiter 106 being threaded allows for easier access to adjusting the exposed length of the drill bit 108 as compared to, for example, a set screw. The depth limiter 106 can be formed from a suitable material. In some examples, the depth limiter 106 is formed from a polymer. In some examples, the depth limiter 106 is formed from ABS.

The depth limiter 106, in certain examples, may also include an adjustment collar 170 for adjusting the length which the drill bit 108 is exposed. The adjustment collar 170 includes a limiter proximal portion 170*a* and a limiter distal portion 170*b*. The limiter proximal portion 170*a* has a width and a length. The width of the limiter proximal portion 170*a* is sufficient to attach to the housing 102 of the surgical bone drill 100 and the length of the limiter proximal portion 170*a* is sufficient to allow a user to easily grasp the depth limiter 106 at least at the limiter proximal portion 170*a*. In certain embodiments, the limiter proximal portion 170*a* includes internal threads 170*d* allowing the adjustment collar 170 to attach to the threading of the sleeve 156 portion. In other examples, the adjustment collar 170 is affixable to the housing 102 via ratcheting or a similar method. The limiter proximal portion 170*a* additionally includes an external grip 170*c* allowing for the limiter proximal portion 170*a* to be easily rotated.

The limiter distal portion 170*b* also includes a width and a length. In some embodiments, the width, and the length of the limiter distal portion 170*b* is less than the width and the length of the limiter proximal portion 170*a*. In certain embodiments, the width, and the length of the limiter distal portion 170*b* are small enough so that the adjustment collar 170 cannot rotate completely onto the sleeve 156. In this way, at least the limiter distal portion 170*b* covers the bit distal portion 126. In some examples, when the adjustment collar 170 is rotated distally to the bit distal end 120, the drill bit 108 is completely covered. Completely covering the bit distal end 120 allows for the surgical bone drill 100 to easily be stored and transported without risking damage to the drill bit 108. In some examples, when the adjustment collar 170 is rotated proximally towards the housing 102 as far as possible, the maximum length of the bit distal portion 126 is exposed. In some examples, the maximum length the bit distal portion 126 is exposed is about 3.5 cm, about 4 cm, about 4.5 cm, about 5 cm or other suitable maximum length. In some examples, the maximum length the bit distal portion 126 is exposed is between about 3.5 cm-0.5 cm, about 3.8 cm-4.7 cm, about 4.1-4.4 cm, or other suitable range. In some examples, the adjustment collar 170 surrounds the bit distal portion 126 of the drill bit 108 that is not exposed, in other examples the adjustment collar 170 surrounds a portion of the bit distal portion 126 that is not exposed. In some embodiments, the drill bit 108 includes permanent markings which show the length exposed of the distal portion 126. The markings can be formed by etching, engraving, laser marking, color marking, or other suitable marking method that does not change the shape of the drill bit. FIG. 5 depicts a drill bit having markings 516 depicting various depths. The markings may represent commonly used depths. In other embodiments, markings are on the housing 102, adjustment collar 170, the sleeve 156 or other suitable location. For example, the markings could be exposed as the depth limiter is rotated showing a user the exposed depth.

In certain embodiments, the limiter distal portion 170*b* is positioned at an angle X relative to the limiter proximal portion 170*a* (see FIG. 3) to allow for the limiter distal portion 170*b* to be smaller than the limiter proximal portion 170*a*. The limiter distal portion 170*b* is relatively smooth and is configured to abut the cranium 200 of a patient (discussed in further detail below). The limiter distal portion 170*b* can additionally assist in spreading the tissue of an incision made in a patient and directly abuts the bone being drilled into. In certain embodiments, the limiter distal portion 170*b* tapers at approximately angle X as at a transition region 170*f* between the limiter distal portion 170*b* and the limiter proximal portion 170*a*. In certain embodiments, the angle X is about 30 degrees, about 35 degrees, about 40 degrees or other suitable angles. In some embodiments, the angle X is between about 30 degrees-40 degrees or about 33 degrees-37 degrees, or other suitable ranges of angles. In some embodiments, when the limiter distal portion 170*b* assist spreading the tissue, the transition region 170*f* or a portion of the taper abuts a patient's scalp 202 while the limiter distal portion 170*b* abuts the skull 206. In other embodiments, the limiter distal portion 170*b* can be stepped down from the limiter proximal portion 170*a* such that the transition region 170*f* is perpendicular with respect to the limiter distal portion 170*b* and the limiter proximal portion 170*a*. In this case, only the limiter distal portion 170*b* abuts the cranium 200 of a patient. In some examples, the limiter distal portion 170*b* has a diameter that is minimally larger than the drill bit 108 allowing the limiter distal portion 170*b* to extend within an incision. In other examples, the limiter distal portion 170*b* can be large and configured to extend around an incision.

In some examples, the depth limiter 106 only includes the adjustment collar 170. In certain other examples, the depth limiter 106 includes a locking nut configured to prevent rotation of the adjustment collar 170 in a proximal direction. In some embodiments, the locking nut can be a nut that rotates up to the proximal end of the adjustment collar 170. In other examples, a ratchet mechanism or other suitable locking device can be used. In some embodiments the locking nut is a locking collar 172. The locking collar 172 is configured to prevent the adjustment collar 170 from rotating once a desired length of exposure of the bit distal is selected. In certain embodiments, the locking collar 172 is attached to the sleeve 156 and rotatable to abut against the adjustment collar 170 thereby preventing the adjustment collar 170 from moving proximally. In certain embodiments, the locking collar 172 includes internal threads 172*a* to rotatably attach to the sleeve 156 however, the locking collar 172 can attach to the sleeve 156 in any other method. For example, the locking collar 172 can include a ratchet mechanism or other suitable lock. In certain embodiments, the locking collar 172 has approximately the same width as the adjustment collar 170. In other embodiments, the locking collar 172 can have a smaller or greater width than the adjustment collar 170. The locking collar 172 additionally includes an exterior grip 172*b* on at least a portion of the exterior thereby allowing the locking collar 172 to be easily gripped and rotated by a user.

FIG. 3 depicts the surgical bone drill 100 being used as a cranial drill to drill a hole in a cranium 200 of a patient. The cranium 200 includes a scalp 202, a skull 206, a dura 208, and a brain 210. The cranium 200 additionally includes a subdural region 212 between the dura 208 and the brain 210. As discussed above, in some cases a subdural hematoma can occur in the subdural region 212 which requires drainage.

In operation, an incision can be made in the scalp 202, in some examples, the incision is relatively small and allows only for the drill bit 108 to extend therethrough. In certain embodiments, the spike 121 creates the incision. In some examples, the scalp 202 can include tissue such as: skin, subcutaneous tissue, galea and periosteum. Depending on the size of the incision, only the drill bit 108 extends through the incision and spreads the tissue of the scalp 202. In other examples, a tissue retractor (e.g., see FIG. 4) can be used to help spread tissue of the scalp 202. In some other examples, the limiter distal portion 170*b* extends into the incision and assists with spreading the tissue of the scalp 202, without the use of a tissue retractor. In another example, the incision is small enough such that only the drill bit 108 spreads the tissue. This allows for the incision to heal quickly and without the need of further medical assistance, for example, stitches.

Once the incision is made, the drill bit 108 can be used to drill a hole through the skull 206 by rotation of the drill bit 108 via the drive mechanism 104. As discussed above, the cutting portion 130 including the cutting tip 123 and flutes of the drill bit 108 are responsible for the cutting work as the drive mechanism 104 rotates the drill bit 108. A pre-selected length of the exposed bit distal portion 126 is drilled through the skull 206. As can be seen in, FIG. 3, the distal end 120 is sharp and pierces the dura 208 thereby allowing for the subdural region 212 to be drained. The limiter distal portion 170*b* is configured to abut the cranium 200. In certain examples, the limiter distal portion 170*b* assists with spreading the tissue of the scalp 202 and abuts the skull 206. In other examples, the limiter distal portion 170*b* is relatively larger and only abuts the scalp 202.

After a hole is drilled into the skull 206, a subdural drainage device, for example the drainage device shown in U.S. Pat. No. 7,694,821, can be used to drain the subdural region 212.

Figure 4:
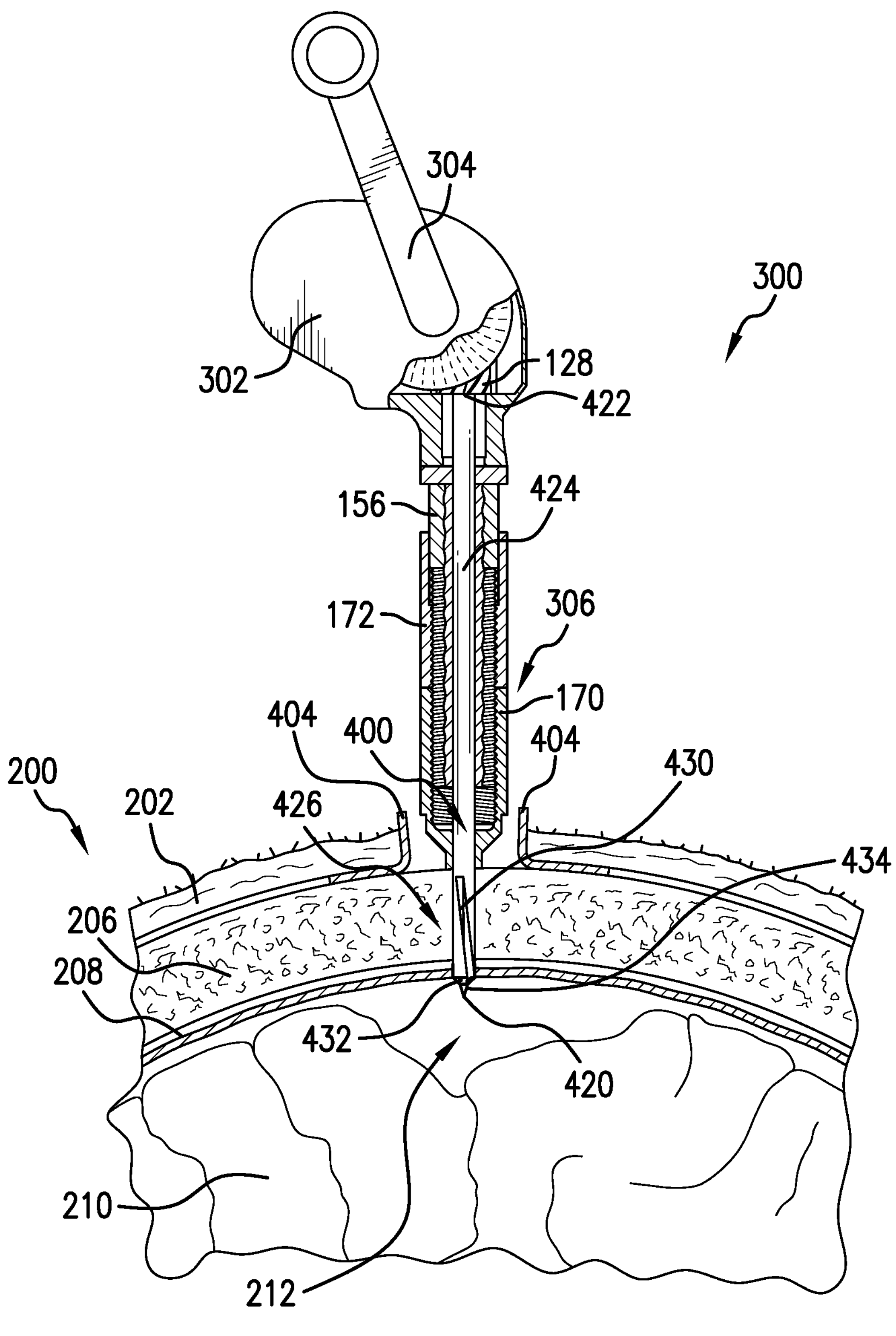
FIG. 4 is a sectional view of an alternative embodiment of the surgical bone drill in use.

Referring to FIG. 4, a surgical bone drill 300 in a different embodiment is described. The surgical bone drill 300 is similar to the surgical bone drill 100 and includes a similar depth limiter 306, a similar housing 302, and a similar drive mechanism 304. However, the surgical bone drill 300 includes a drill bit 400 that is configured differently than the drill bit 108. The drill bit 400, similar to the drill bit 108, allows for enhanced grip of the surgical bone drill 300 on the skull 206 of a patient when in use and is similarly configured to pierce the dura 208 of a patient (discussed in greater detail below) when drilled through the patient's skull 206. In some examples, the drill bit 400 is configured as a cranial drill bit.

The drill bit 400 comprises a longitudinal body extending along an axis and having a distal end 420 and a proximal end 422 such that the drill bit 400 extends between the distal end 420 and the proximal end 422. The drill bit 400 includes spiral flute(s) formed around the body and extending from a cutting tip 432 along the axis of the body. The drill bit 400 includes a bit proximal portion 424 towards the proximal end 422.

The drill bit 400 additionally includes a bit distal portion 426 towards the distal end 420. The bit distal portion 426 includes a cutting portion 430 similar to the cutting portion 130 In some examples, the cutting tip 432 that is a convex conical tip. The drill bit 400 additionally includes a spike 434 that extends from the cutting tip 432 and terminates at the distal end 420. The spike 434 comes to a point as it reaches the distal end 420 and functions similar to the spike 121 discussed above. In some examples the spike 434 is a conical spike 434 that comes to a sharp point. In some examples, the spike 434 includes the cutting flute.

Referring again to FIG. 4, the surgical bone drill 300 is being used as a cranial drill to drill a hole in a cranium 200 of a patient (the cranium includes substantially the same parts as shown in FIG. 3). An incision has been made in the scalp 202 and tissue of the scalp 202 is being held open by a tissue retractor 404. In some examples, the tissue retractor 404 is a "Holzheimer" retractor. In other examples, the tissue retractor 404 is a "Mastoid" retractor, or a "Gelpi" retractor or a "Heiss" retractor. It will be appreciated that the surgical bone drill 300 can be used without the retractor in a similar method to that of FIG. 3. It will also be appreciated that the surgical bone drill 100 can be used with a tissue retractor 404 similarly to the surgical bone drill 300 of FIG. 4.

The drill bit 400 can drill a hole through the skull 206 by rotation of the drill bit 400 via the drive mechanism 304 through the cutting portion 430 including the cutting tip 432 and flutes. In examples where the spike 434 includes the flutes, the spike 434 can also assist in the cutting work. Similarly, to the above example, a pre-selected length of the bit distal portion 426 is selected, and the depth limiter 306 is adjusted accordingly. As the drill bit 400 reaches the dura 208, spike 434 pierces the dura 208.

Referring to FIG. 5, a kit 500 includes a surgical drill 510 having a depth limiter 512. The drill 510 and depth limiter 512 are similar to the drills 100, 300 discussed throughout. The kit 500 stores the components in a container 525. The container 525 may include indentations 526 which facilitate removal of the components stored within. The indentations 526 are optional and may or may not be included. The container 525 may be a suitable device for safe transportation of the drill 510 and parts included.

The drill 510 includes a motorized drive mechanism (as discussed above). The kit further includes a charging mechanism 514. As depicted, the charging mechanism includes a charging cable, such as a USB C to USB A cable. The drill 510 is depicted as being completely assembled with an exposed drill bit. It will be appreciated that in other examples, the drill may require assembly, the drill bit may be covered (as discussed above) or presented in a different suitable manner allowing for safe delivery of the drill 510.

In certain embodiments, the kit 500 additionally includes devices for use in conjunction with the drill 510, such as for draining a subdural hematoma. For example, the kit 500 includes a subdural evacuation port device 520. The subdural evacuation port device 520 can be a suitable subdural evacuation port device, for example the subdural evacuation device shown in U.S. Pat. No. 7,694,821; the subdural evacuation device shown in co-pending U.S. application Ser. No. 18/347,474 entitled "Subdural Evacuation Port with Needle Access Port"; Ser. No. 18/347,515 entitled "Transparent Surgical Evacuation Port Device"; or 63/611,728 entitled "Surgical Evacuation Port Device with Sealing Device." Each of which are incorporated herein by reference.

The kit 500 additionally includes devices useful for draining the subdural space in cooperation with the subdural evacuation port device 520. The kit 500 includes a tap 530 which is configured to create threading within a hole that is created by the drill 510. Threads created by the tap 530 can, for example, facilitate connection with a skull engagement region 522 of the subdural evacuation port device 520. In other examples, any other devices useful in connection with the hole may be used, for example, other drainage devices, devices for extracting marrow from a bone, devices for providing nutrients to a bone or other suitable devices.

The kit may also include a conduit 540 to, for example, connect the subdural evacuation port device 520 to a negative pressure device 550. In some embodiments, the conduit connects to a fitting 524 on the subdural evacuation port device 520. The negative pressure device 550 is additionally included in the kit 500 and can be any device capable of providing negative pressure through the conduit 540. As depicted, the negative pressure device 550 is a bulb pump. The negative pressure device 550 may also be an electrical pump, other manual pump such as a Hemovac or Blake drain. Further details related to the usage of the subdural evacuation port device 520 along with more specific details of the subdural evacuation port device are disclosed in the patents referred to above.

In certain embodiments, the kit comprises instructional material. In certain embodiments, the instructional material includes a publication, a recording, a diagram, or any other medium of expression which can be used to communicate the usefulness of the device described herein. The instructional material of the kit of the disclosure, for example, can be affixed to a package which contains one or more instruments which may be necessary for the desired procedure. Alternatively, the instructional material is shipped separately from the package, or is accessible electronically via a communications network, such as the Internet.

In one embodiment, the disclosure includes a kit for portable use. To facilitate portable use, a kit of the present disclosure may further include a razor or clipper for removing hair from a subject, a ruler or tape measure for measuring the location of a site for incision, a surgical marker or other implement for marking the site of incision, skin preparation material (i.e., antiseptic, alcohol pads) to clean the site of incision, and any additional surgical and medical elements that may be useful for such an operation, such as surgical tape, gauze, bandages, surgical thread and needle, and the like.

Other advantages of the present invention can be apparent to those skilled in the art from the foregoing specification. Accordingly, it will be recognized by those skilled in the art that changes, or modifications may be made to the above-described embodiments without departing from the broad inventive concepts of the invention. It should therefore be understood that this invention is not limited to the particular embodiments described in this document but is intended to include all changes and modifications that are within the scope and spirit of the invention as defined in the claims.

The term "approximately," when used in connection with a numeric value, is intended to include values that are close to, but not exactly, the number. For example, in some embodiments, the term "approximately" may include values that are within +/−5 percent of the value.

This disclosure is not limited to the particular systems, methodologies or protocols described, as these may vary. The terminology used in this description is for the purpose of describing the particular versions or embodiments only and is not intended to limit the scope. It will be understood that terms such as "same," "equal," "planar," or "coplanar," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to emphasize this meaning, unless the context or other statements clearly indicate otherwise. For example, items described as "substantially the same," "substantially equal," or "substantially planar," may be exactly the same, equal, or planar, or may be the same, equal, or planar within acceptable variations that may occur, for example, due to manufacturing processes and/or tolerances. The term "substantially" may be used to encompass this meaning, especially when such variations do not materially alter functionality. As used herein, the term "proximal" means closest to the operator (less into the body) and "distal" means furthest from the operator (further into the body). In positioning a medical device from a downstream access point, distal is more upstream and proximal is more downstream. It will be understood that various modifications may be made to the embodiments disclosed herein. Likewise, the above disclosed methods may be performed according to an alternate sequence. Therefore, the above description should not be construed as limiting, but merely as exemplification of the various embodiments. Those skilled in the art will envision other modifications within the scope and spirit of the claims appended hereto.

What is claimed is:

1. A surgical bone drill, comprising:

a housing;

a drill bit comprising:

a bit proximal portion that is mounted within the housing, and a bit distal portion that extends distally from the housing and includes a cutting tip configured to drill into bone of a patient;

a depth limiter having a limiter distal-end positioned adjacent the bit distal portion and an aperture configured to coaxially receive the bit distal portion and closely surround the drill bit with minimal clearance therebetween, the depth limiter being operatively coupled to the housing such that rotation of the depth limiter causes a change in an exposed length of the bit distal portion that extends beyond the limiter distal-end, thereby limiting a depth that the drill bit is able to drill into the bone, the depth limiter being rotatable on the housing over a plurality of rotations without locking; and a drive mechanism disposed within the housing and operably connected with the bit proximal portion of the drill bit to rotate the drill bit to drill into the bone.

2. The surgical bone drill of claim 1, wherein:

the housing includes a sleeve having sleeve threads, the sleeve being configured to receive the bit proximal portion; and the depth limiter is threaded to the sleeve threads to select the exposed length of the bit distal portion that extends beyond the limiter distal-end, the depth limiter being rotatable on the sleeve threads over the plurality of rotations without locking.

3. The surgical bone drill of claim 2, wherein:

the depth limiter further comprises a locking device configured to lock the depth limiter in a desired position on the sleeve; and the locking device is configured to be selectively disengaged to allow rotation of the depth limiter.

4. The surgical bone drill of claim 3, wherein the desired position on the sleeve is selected from a plurality of angular positions corresponding to one or more complete clockwise or counterclockwise revolutions of the depth limiter on the sleeve threads.

5. The surgical bone drill of claim 3, wherein the locking device comprises:

a locking nut threaded to the sleeve threads and configured to prevent the rotation of the depth limiter on the sleeve after the exposed length of the bit distal portion is selected.

6. The surgical bone drill of claim 1, wherein the cutting tip is a convex conical cutting tip with a spike extending distally from the cutting tip, the spike being sufficiently sharp to pierce a dura of the patient.

7. A surgical kit comprising:

the surgical bone drill of claim 1; and one or more devices for evacuation of fluid from a subdural space of the patient.

8. The surgical kit of claim 7, wherein the one or more devices for evacuation of fluid from the subdural space include:

a subdural evacuation port device; and a negative pressure device.

9. The surgical kit of claim 7, further comprising a tap for creating threads within a hole created by the drill.

10. The surgical bone drill of claim 1, wherein the depth limiter is configured to be rotatably adjusted over the plurality of rotations from a first position on the housing to a second position on the housing without unlocking a locking device.

11. The surgical bone drill of claim 1, wherein the depth limiter is configured to be rotatably removed from the housing without unlocking a locking device.

12. The surgical bone drill of claim 1, wherein:

the housing includes housing threads; and the depth limiter is configured to be threaded to the housing threads to select the exposed length of the drill bit, the depth limiter being rotatable on the housing threads over a plurality of rotations without locking.

13. The surgical bone drill of claim 12, wherein:

the depth limiter further comprises a locking device configured to lock the depth limiter in a desired position on the housing; and the locking device is configured to be selectively disengaged to allow free rotation of the depth limiter.

14. A surgical bone drill, comprising:

a housing;

a drill bit including:

a bit proximal portion that is mounted within the housing, and a bit distal portion that extends distally from the housing and includes a cutting tip configured to drill into bone of a patient;

a depth limiter having a limiter distal-end positioned adjacent the bit distal portion, the depth limiter being operatively coupled to the housing such that rotation of the depth limiter causes a change in an exposed length of the bit distal portion that extends beyond the limiter distal-end, thereby limiting a depth that the drill bit is able to drill into the bone, the depth limiter being rotatable on the housing over a plurality of rotations without locking, wherein the depth limiter includes:

a limiter distal portion that includes the limiter distal-end and having a first height and a first outer width, the limiter distal portion positioned adjacent the bit distal portion and configured to abut a first surface of the patient, a limiter proximal portion having a second height and a second outer width, and wherein the first height and the first outer width are less than the second height and the second outer width, respectively; and a drive mechanism disposed within the housing and operably connected with the bit proximal portion of the drill bit to rotate the drill bit to drill into the bone.

15. A surgical bone drill, comprising:

a housing;

a drill bit including:

a cutting tip configured to drill into bone of a patient, and a cutting portion positioned proximal to the cutting tip, the cutting portion defining a drill bit diameter large enough to drill a first hole in the bone;

a depth limiter mounted to the housing, the depth limiter configured to select an exposed length of the drill bit that extends beyond the depth limiter, the depth limiter including:

a limiter distal portion positioned adjacent the exposed length of the drill bit, having:

a distally facing surface positioned to abut a first surface of the patient, thereby limiting a depth that the drill bit is able to drill into the bone, an aperture having an inner diameter and configured to coaxially receive the cutting portion, the inner diameter being configured to closely approximate the drill bit diameter with minimal clearance therebetween, and a first outer width and a first height, and a limiter proximal portion having a second outer width and a second height, the first outer width and the first height being smaller than the second outer width and the second height, respectively; and a drive mechanism operably connected with a proximal portion of the drill bit to rotate the drill bit to cause the drill bit to drill into the bone.

16. The surgical bone drill of claim 15, wherein the limiter proximal portion is adjustable with respect to the housing to select the exposed length of the drill bit that is exposed beyond the depth limiter.

17. The surgical bone drill of claim 15, wherein:

the housing includes a sleeve having sleeve threads, the sleeve being configured to receive a bit proximal portion of the drill bit; and the depth limiter includes an adjustment collar that is threaded to the sleeve threads to select the exposed length of the drill bit, the adjustment collar being rotatable on the sleeve threads over a plurality of rotations without locking.

18. The surgical bone drill of claim 17, wherein:

the depth limiter further comprises a locking device configured to lock the depth limiter in a desired position on the sleeve; and the locking device is configured to be selectively disengaged to allow free rotation of the depth limiter.

19. The surgical bone drill of claim 15, wherein the drill bit includes a bit distal portion including a convex conical cutting tip with a spike extending distally from the cutting tip, the spike being sufficiently sharp to pierce a dura of the patient.

20. The surgical bone drill of claim 15, wherein the drill bit further comprises:

a bit proximal portion that is mounted within the housing;

a bit distal portion that extends distally from the housing; and wherein the depth limiter surrounds the bit distal portion.

21. The surgical bone drill of claim 15, wherein:

the first surface of the patient is a scalp; and the first outer width is large enough to abut the scalp without entering an incision made in tissue adjoining the bone being drilled into.

22. The surgical bone drill of claim 15, wherein the depth limiter tapers in a transition region defined between the second outer width and the first outer width.

23. The surgical bone drill of claim 15, wherein the depth limiter is stepped at a transition region defined between the second outer width and the first outer width.

* * * * *